United States Patent [19]

Klein et al.

US005328900A

[11] Patent Number: 5,328,900
[45] Date of Patent: * Jul. 12, 1994

[54] ANTI-THROMBOTIC PEPTIDE AND PSEUDOPEPTIDE DERIVATIVES

[75] Inventors: Scott I. Klein, Audubon; Bruce F. Molino, Hatfield, both of Pa.

[73] Assignee: Rhone-Poulenc Rorer Pharmaceuticals Inc., Collegeville, Pa.

[*] Notice: The portion of the term of this patent subsequent to Nov. 12, 2008 has been disclaimed.

[21] Appl. No.: 961,216

[22] Filed: Oct. 15, 1992

Related U.S. Application Data

[63] Continuation of Ser. No. 724,675, Jul. 2, 1991, abandoned, which is a continuation-in-part of Ser. No. 505,286, Apr. 5, 1990, Pat. No. 5,064,814.

[51] Int. Cl.[5] .................. A61K 37/02; C07K 5/00
[52] U.S. Cl. .................................. 514/18; 514/19; 530/331; 540/597; 540/602; 546/208
[58] Field of Search ............. 514/18, 19; 530/331; 540/597, 602; 546/208

[56] References Cited

U.S. PATENT DOCUMENTS 5,064,814 11/1991 Klein et al. .................. 514/18

Primary Examiner—Lester L. Lee
Attorney, Agent, or Firm—Paul R. Darkes; Martin F. Savitzky

[57] ABSTRACT

Disclosed are novel peptide and pseudopeptide derivatives and pharmaceutical compositions thereof that inhibit platelet aggregation and thrombus formation in mammalian blood.

16 Claims, No Drawings

ANTI-THROMBOTIC PEPTIDE AND PSEUDOPEPTIDE DERIVATIVES

This application is a continuation application of co-pending U.S. application Ser. No. 07/724,675 filed Jul. 2, 1991 now abandoned, which is, in turn, a continuation-in-part of application Ser. No. 07/505,286, filed Apr. 5, 1990 now U.S. Pat. No. 5,064,814.

BACKGROUND OF THE INVENTION

1. Field of the Invention

This invention relates to novel compounds having anti-thrombotic activity. More particularly, the invention relates to novel peptide and pseudopeptide derivatives that inhibit platelet aggregation and thrombus formation in mammalian blood thereby being useful in the prevention and treatment of thrombosis associated with certain disease states, such as, myocardial infarction, stroke, peripheral arterial disease and disseminated intravascular coagulation.

Haemostasis, the biochemistry of blood coagulation, is an extremely complex and as yet not completely understood phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of platelet adhesive glycoproteins, i.e., fibrinogen, fibronectin, and von Willebrand factor. Fibrinogen is a co-factor for platelet aggregation, fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane glycoprotein complex IIb/IIIa.

Adhesive glycoprotein, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. The novel molecules described in this invention may block the fibrinogen receptor, thus inhibiting platelet aggregation and subsequent thrombus formation. Pharmaceutical agents and/or compositions possessing such an inhibiting effect may be provided for the prophylaxis and treatment of thrombogenic diseases, such as myocardial infarction, stroke, peripheral arterial disease and disseminated intravascular coagulation.

2. Reported Developments

It has been observed that the presence of Arg-Gly-Asp (RGD) is necessary in fibrinogen, fibronectin and von Willebrand factor for their interaction with the cell surface receptor (Ruoslahti E., Pierschbacher, Cell 1986, 44,517-18). Two other amino acid sequences also seem to take part in the platelet attachment function of fibrinogen, namely, the Gly-Pro-Arg sequence, and dodecapeptide, His-His-Leu-Gly-Gly-Ala-Lys-Gln-Ala-Gly-Asp-Val, sequence. Synthetic small peptides containing the RGD or dodecapeptide units show activity: they bind to the platelet receptor and competitively inhibit binding of fibrinogen, fibronectin and von Willebrand factor as well as inhibiting aggregation of activated platelets (Plow et al. Proc. Natl. Acad. Sci. USA 1985, 82, 8057-61; Ruggeri et al. Proc. Natl. Acad. Sci. USA 1986, 5708-12; Ginsberg et al. J. Biol. Chem. 1985, 260, 3931-36; and Gartner et al. J. Biol. Chem. 1987, 260, 11,891-94 ).

The present invention is directed to novel peptide and pseudopeptide derivatives that inhibit platelet aggregation and subsequent thrombus formation.

SUMMARY OF THE INVENTION

The present invention comprises N-amidino-piperidine carboxyl cyclic amino acid derivatives of the general formula:

$$\begin{array}{c}(CH_2)_m \quad O \quad (CH_2)_n \quad O \quad O \\ \overset{|}{\underset{N}{\bigg|}} - C - N - \overset{|}{\underset{}{\bigg|}} - C - NH - CH - C - Y \\ \underset{X}{N} \qquad\qquad\qquad\qquad (CH_2)_p \\ \qquad\qquad\qquad\qquad\qquad COOH \end{array}$$

wherein:

X is H, amidino,

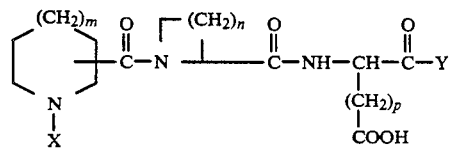

Y is —OR$_1$,

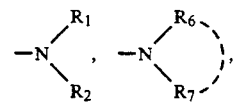

a D- or L-amino acid or its corresponding carboximide, a synthetic amino acid of the formula

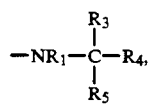

a dipeptide or a dipeptide isostere of the formula

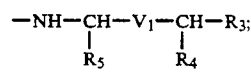

R$_1$ and R$_2$ are independently H, alkyl, aryl, aralkyl, or allyl;

R$_3$ is H, —CO$_2$H, —CO$_2$R$_1$, —CONH$_2$,

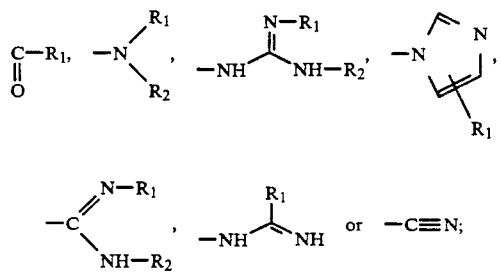

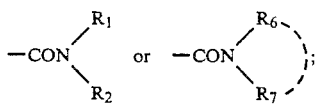

$R_4$ and $R_5$ are independently H, alkyl, cycloalkyl, cycloalkylmethyl,

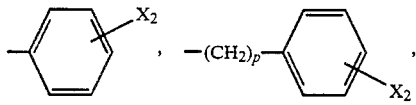

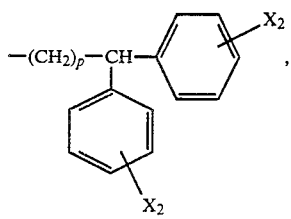

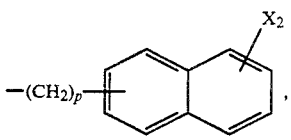

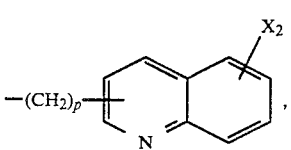

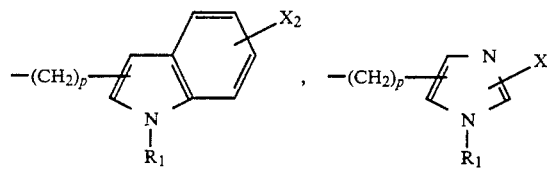

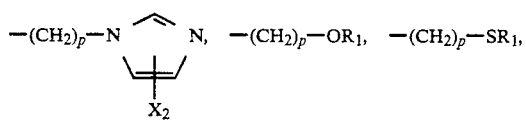

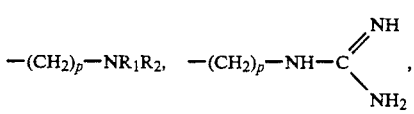

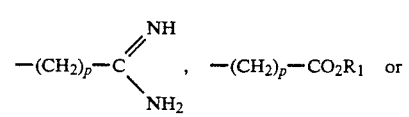

$R_6$ and $R_7$ form a ring with the nitrogen to which they are attached and are $-(CH_2)_4-$, $(CH_2)_5-$, $-(CH_2)_6-$, $-CH_2CH_2OCH_2CH_2-$, $-CH_2CH_2NR_1CH_2-$ or

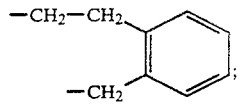

$X_2$ is H, Cl, Br, F, $-OR_1$, $-NO_2$,

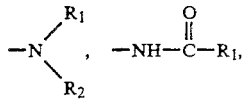

$-SR_1$, $C_1-C_5$ alkyl, phenyl, $-CO_2R_1$,

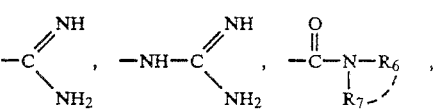

$-CF_3$ or $-NHSO_2R_1$;

$V_1$ is

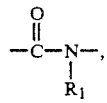

$-(CH_2)_n-$, $-CH=CH-$, $-CH_2-NH-$, $-CH_2-O-$, $-CH_2-S-$ or

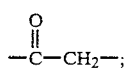

m is 0, 1 or 2;
n is 0, 1, 2, 3 or 4;
p is 0, 1, 2 or 3; and
pharmaceutically acceptable salts thereof.

In accordance with the present invention, novel compounds are provided which inhibit platelet aggregation by inhibiting fibrinogen binding to activated platelets and other adhesive glycoproteins involved in platelet aggregation and blood clotting. Compounds of the present invention, as tested by methods predictive of antithrombotic activity, are believed to be useful in the prevention and treatment of thrombosis associated with certain diseased states, such as myocardial infarction, stroke, peripheral arterial disease and disseminated intravascular coagulation.

The present compounds may also be useful for the treatment of certain cancerous diseases since they may interfere with adhesive interactions between cancer cells and the extracellular matrix (Journ. of Biol. Chem., Vol. 262, No. 36 1987, pp. 17703-17711; Science, Vol. 233, 1986, pp. 467-470; and Cell, Vol. 57, 59-69, April 1989).

The invention also comprises pharmaceutical compositions useful for the prevention and treatment of thrombosis comprising an aforesaid compound in a pharmaceutically acceptable carrier.

Another aspect of this invention comprises a method for the prevention and treatment of thrombosis associated with the aforesaid diseases.

DETAILED DESCRIPTION OF THE INVENTION

In accordance with the present invention, novel compounds are provided which inhibit platelet aggregation by inhibiting fibrinogen binding and other adhesive glycoproteins involved in platelet aggregation and blood clotting to activated platelets. Compounds of the present invention, as tested by methods predictive of anti-thrombotic activity, are believed to be useful in the prevention and treatment of thrombosis associated with certain disease states, such as myocardial infarction, stroke, peripheral arterial disease and disseminated intravascular coagulation.

The present compounds may also be useful for the treatment of certain cancerous diseases since they may interfere with adhesive interactions between cancer cells and the extracellular matrix (Journ. of Biol. Chem., Vol. 262, No. 36 1987, pp. 17703-17711; Science, Vol. 233, 1986, pp. 467-470; and Cell, Vol. 57, 59-69, April 1989).

As used above and throughout the description of this invention, the following terms, unless otherwise indicated, shall be understood to have the following meanings:

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain. Preferred alkyl groups are the "lower alkyl" groups which are those alkyl groups having from 1 to about 6 carbons. Alkyl may be substituted by other moieties such as halogen or alkoxy.

"Halogen" means Cl, Br, I or F.

"Alkoxy" means an alkyl-O— group. Lower alkoxy groups are preferred. Exemplary groups include methoxy, ethoxy, n-propoxy, i-propoxy and n-butoxy.

"Aryl" means a mononuclear and polynuclear aromatic hydrocarbon radical which can be substituted or unsubstituted in one or more positions. Examples of aryl groups include phenyl, naphthyl, anthranyl, phenanthranyl, azulyl and the like which can be substituted with one or more of the substituents. Aryl is preferrably substituted or unsubstituted phenyl or naphthyl. Aryl substituents include hydrogen, alkyl, alkoxy, amino, halo, aryl, aryloxy, carboalkoxy, nitro, dialkylamino, trifluoromethyl, thioalkyl and carbamoyl.

"Aralkyl" means an alkyl group substituted by an aryl radical, wherein "aryl" means a phenyl or phenyl substituted with one or more substituents which may be alkyl, alkoxy, amino, nitro, carboxy, carboalkoxy, cyano, alkylamino, halo, hydroxy, hydroxyalkyl, mercapto, alkylthio, acyl or carbamoyl. Exemplary groups include benzyl and phenethyl.

"Carboalkoxy" means an

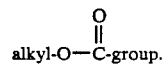

Preferred carboalkoxy groups are those in which the alkyl group is lower alkyl.

"Alkylamino" means an alkyl-NH— group. Preferred groups are lower alkylamino groups.

"Alkylthio" means an alkyl-S— group. Preferred groups are lower alkylthio.

"Acyl" means an

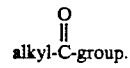

Preferred acyl groups are those in which the alkyl group is lower alkyl.

D- and L-amino acids include: Asp, Arg, Ala, Asn, Cys, Gly, Glu, Gln, His, Ile, Leu, Lys, Met, Orn, Phe, Pro, Ser, Thr, Trp, Tyr and Val.

Stereoisomers and diastereomers of the compounds covered by the general formula also constitute a part of the present invention and intended to be covered by the appended claims.

The compounds of the present invention may be readily prepared by standard solid phase or solution phase peptide synthesis techniques using starting materials and/or intermediates available from chemical supply companies such as Aldrich and Sigma or or may be synthesized by standard organic chemical techniques. (H. Paulsen, G. Merz, V. Weichart, "Solid-Phase Synthesis of O-Glycopeptide Sequences", Angew. Chem. Int. Ed. Engl. 27 (1988); H. Mergler, R. Tanner, J. Gosteli, and P. Grogg, "Peptide Synthesis by a Combination of Solid-Phase and Solution Methods I: A New Very Acid-Labile Anchor Group for the Solid-Phase Synthesis of Fully Protected Fragments. Tetrahedron letters 29, 4005 (1988); Merrifield, R. B., "Solid Phase Synthesis After 25 Years: The Design and Synthesis of Antagonists of Glucagon", Makromol. Chem. Macromol. Symp. 19, 31 (1988).

The solid phase method is represented schematically as follows:

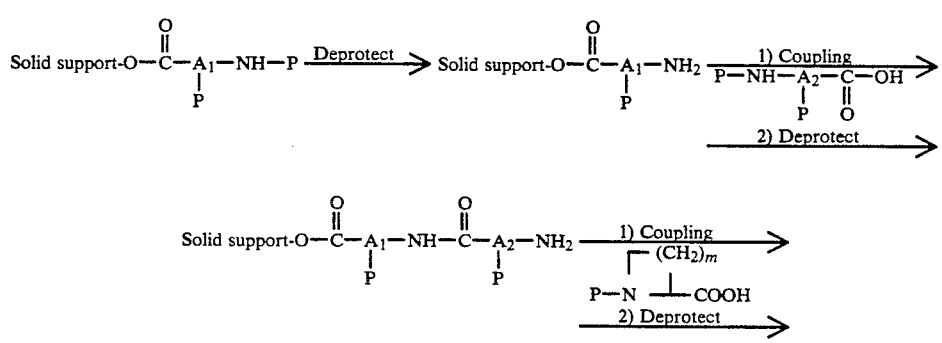

-continued

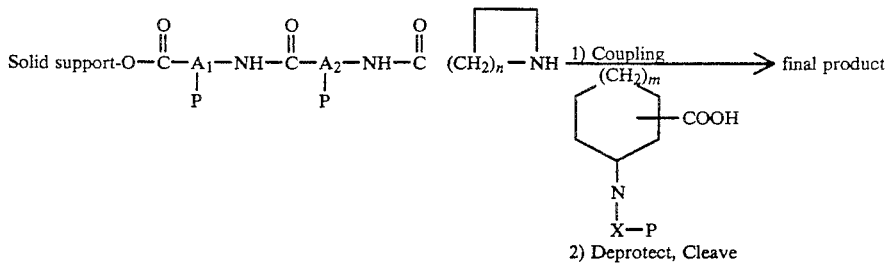
2) Deprotect, Cleave wherein: the solid support may be, but is not limited to, p-alkoxybenzyl resin;

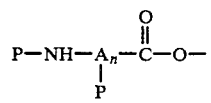

is a protected amino acid derivative;

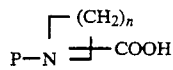

is a protected derivative of a nitrogen heterocycle carboxylic acid where n may be 0, 1, 2, 3 or 4; and

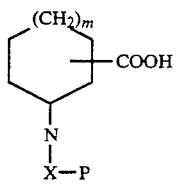

is a protected derivative of a nitrogen heterocycle carboxylic acid where X is H, amidino or

where $R_1$ is alkyl, aryl or aralkyl; and
m is 0, 1 or 2.

In the process of making the desired compound, the amino acid derivatives are added one at a time to the insoluble resin to give the desired dipeptide resin derivative, then the nitrogen heterocycles are likewise coupled, in turn, to the N-terminal of the chain. Any reactive functional groups of these derivatives are blocked by protecting groups to prevent cross reactions during the coupling procedures. These protecting groups include, but are not limited to, tertiary butoxycarbonyl (BOC), carbobenzoxy (CBZ), benzyl, t-butyl, 9-fluorenylmethoxycarbonyl (FMOC), hydrogen chloride and methoxy-2,3,6-trimethylbenzenesulfonyl (MTR).

Upon completion of each coupling reaction, the $\alpha$-amino protecting group is removed by standard procedures and, the $\alpha$-amino group is, in turn, coupled to a derivative having a free carboxylic acid function. This procedure is repeated until the desired product derivative is formed. The final product is obtained by deprotection and cleavage of the product from the resin by standard techniques.

Alternatively, the compounds of the present invention may be prepared in solution, i.e., without using a solid support. In a manner that is similar to the solid phase synthesis, the protected amino acids are coupled, then deprotected using standard procedures.

The invention will now be explained further by the following illustrative examples:

EXAMPLE 1

N-[2(S)-1-(piperidin-4-yl-carbonyl)azetidin-2-yl-carbonyl]-L-aspartyl-L-valine

A. 0.40 g N-(9-fluorenylmethoxycarbonyl)-L-valine-p-alkoxy-benzyl resin ester (containing approximately 0.224 mmol of amino acid) was deprotected by shaking with 10 ml of a solution of 20% piperidine in dimethylformamide for 1 hour. The mixture was filtered and the resin derivative washed with methylene chloride to give L-valine-p-alkoxy-benzyl resin ester.

B. The product from Example 1A was shaken with 0.368 g N-FMOC-L-aspartic acid-b-t-butyl ester, 0.171 g 1-(3-dimethyl-aminopropyl)-3-ethyl carbodiimide hydrochloride (EDC), 0.091 g 1-hydroxybenzotriazole (HOBT), and 0.10 ml of triethylamine in 10 ml of dimethylformamide for 1.5 hours. The mixture was filtered and the resin derivative washed with methylene chloride. The resin derivative was then deprotected as in Example 1A to give L-aspartyl-$\beta$-t-butyl ester-L-valine-p-alkoxy benzyl resin ester.

C. To a solution of 0.50 g of (S)-2-azetidine carboxylic acid in 15 ml of 10% aqueous sodium carbonate solution was added 1.3 g of 9-fluorenylmethylchloroformate in 10 ml of dioxane, dropwise, while maintaining the temperature of the reaction mixture at 0° C. The reaction mixture was allowed to warm to room temperature and stirred for 3 hours, then poured into water and the aqueous solution washed with ether. The aqueous layer was cooled to 0° C. and adjusted to a pH of 2 with 3N hydrochloric acid and extracted with ethyl acetate. The ethyl acetate solution was dried over magnesium sulfate, filtered, and evaporated in vacuo to give (S)-N-(9-fluorenylmethoxycarbonyl)azetidine-2-carboxylic acid.

D. The product from Example 1B was shaken with 0.217 g (S)-N-FMOC azetidine-2-carboxylic acid, 0.128 g EDC, 0.091 g HOBT and 0.1 ml of triethylamine in 10 ml of dimethylformamide for 3 hours at room temperature. The mixture was filtered, washed, and the resin derivative deprotected, as in Example 1B to give N-[(S)-azetidin-2-yl-carbonyl]-L-aspartyl-62 -t-butyl ester-L-valine-p-alkoxy benzyl resin ester.

E. 1.29 g piperidine-4-carboxylic acid and 2.76 g potassium carbonate were combined in 100 ml of 50% aqueous tetrahydro-furan and 2.18 g di-t-butyldicarbonate was added. The mixture was stirred vigorously for 17 hours. The mixture was evaporated in vacuo to remove the tetrahydrofuran, then acidified with 1N hydrochloric acid and the mixture extracted with ethyl acetate. The ethyl acetate solution was dried over sodium sulfate, filtered and evaporated to give N-t-butoxy-carbonyl-piperdine-4-carboxylic acid.

F. The product from Example 1D was shaken with 0.205 g N-BOC-piperidine-4-carboxylic acid, 0.171 g EDC, 0.091 g EDC, 0.091 g HOBT and 0.1 ml triethylamine in 10 ml of dimethylformamide for 2 hours at room temperature. The mixture was filtered and the resin derivative washed with methylene chloride. The resin derivative was deprotected, and the product cleaved from the resin, by treating with 10 ml of 95% trifluoroacetic acid for 2 hours. The resin was removed by filtration and the filtrate diluted with 0.5N aqueous acetic acid. The diluted filtrate was washed with ethyl acetate and lyophilized to give N-[2(S)-1-(piperidin-4-yl-carbonyl)azetidin-2-yl-carbonyl]-L-aspartyl-L-valine as the trifluoroacetate salt; m.p. 86°–88° C.

EXAMPLE 2

N-[2(S)-1-(amidinopiperidin-4-yl-carbonyl)-azetidin-2-yl-carbonyl]-L-aspartyl-L-valine A. N-amidino-4-piperidine carboxylic acid was prepared essentially by the method of Miller, et al., *Synthesis*, 777 (1986), which is incorporated herein by reference. To a solution of 1 g of isonipecotic acid in 10 ml of water was added 1.07 g potassium carbonate and this was stirred for 15 minutes at room temperature. 0.961 g aminoiminomethanesulfonic acid was then added portionwise over 20 minutes. The solution was stirred for 2 hours at room temperature, concentrated in vacuo to one-half of the original volume and the resulting precipitate collected by filtration. The resulting solid was recrystallized from water to give N-amidino-4-piperidine carboxylic acid. This was dissolved in an aqueous solution of tetrahydrofuran. To this solution was added 1 equivalent of 1N hydrogen chloride in ether. The resulting mixture was concentrated in vacuo to give N-amidino-4-piperidine carboxylic acid hydrochloride.

B. N[(S)-azetidin-2-yl-carbonyl]-6-aspartyl-$\beta$-t-butyl ester-L-valine-p-alkoxybenzyl resin ester (prepared from 0.5 g N-FMOC-L-valine-p-alkoxybenzyl resin ester in the manner of Examples 1A, B, C and D) was shaken with 0.24 g N-amidino-piperidine-4-carboxylic acid hydrochloride, 0.222 g EDC, 0.157 g HOBT and 0.16 ml triethylamine in 10 ml dimethylformamide for 3 hours at room temperature. The mixture was filtered and the resin derivative washed with methylene chloride. The product was deprotected, cleaved from the resin and isolated as in Example 1F to give N-[2(S)-1-(1-amidinopiperidin-4-yl-carbonyl)-azetidin-2-yl-carbonyl)]-L-aspartyl-L-valine as the trifluoroacetate salt.

EXAMPLE 3

N-[2(S)-1-(piperidin-3-yl-carbonyl)-azetidin-2-yl-carbonyl]-L-aspartyl-L-valine

A. When piperidine-3-carboxylic acid was substituted for piperidine-4-carboxylic acid and treated as in Example 1E, N-t-butoxycarbonyl-piperidine-3-carboxylic acid was obtained.

B. If N-BOC-piperidine-3-carboxylic acid is substituted for N-BOC-piperidine-4-carboxylic acid in Example 1F and treated in a manner similar to that of that in 1 F, then N-[2(S)-1-(piperidin-3-yl-carbonyl)azetidin-2-yl-carbonyl]-L-aspartyl-L-valine can be obtained.

EXAMPLE 4

N-[1-(piperidin-4-yl-carbonyl)-piperidin-2-yl-carbonyl]-L-aspartyl-L-valine

A. When piperidine-2-carboxylic acid was substituted for (S)-2-azetidine carboxylic acid in Example 1C and treated in a manner similar to that of Example 1C, N-(9-fluorenylmethoxycarbonyl)piperidine-2-carboxylic acid was obtained.

B. When N-FMOC-piperidine-2-carboxylic acid was substituted for the carboxylic acid in Example 1D, N-(piperidin-2-yl-carbonyl)-L-aspartyl-$\beta$-t-butyl ester-L-valine-p-alkoxy benzyl ester resin was obtained.

C. If the product from Example 4B is substituted for the product from Example 1D and treated in a manner similar to that of Example 1F, then N-[1-(piperidin-4-yl-carbonyl)-piperidin-2-yl-carbonyl]-L-aspartyl-L-valine can be prepared.

Utilizing analogous procedures described in Examples 1–4, the following compounds are made:

Pyrrolidine-3-carboxyl-azetidine-2-carboxyl-aspartyl-valine;
pyrrolidine-3-carboxyl-azetidine-2-carboxyl-aspartyl-leucine;
pyrrolidine-3-carboxyl-azetidine-2-carboxyl-aspartyl-isoleucine;
pyrrolidine-3-carboxyl-prolyl-aspartyl-valine;
pyrrolidine-3-carboxyl-prolyl-aspartyl-leucine;
pyrrolidine-3-carboxyl-prolyl-aspartyl-isoleucine;
pyrrolidine-3-carboxyl-piperidine-2-carboxyl-aspartyl-valine;
pyrrolidine-3-carboxyl-piperidine-2-carboxyl-aspartyl-leucine;
pyrrolidine-3-carboxyl-piperidine-2-carboxyl-aspartyl-isoleucine;
N-amidinopyrrolidine-3-carboxyl-azetidine-2-carboxyl-aspartyl-valine;
N-amidinopyrrolidine-3-carboxyl-azetidine-2-carboxyl-aspartyl-leucine;
N-amidinopyrrolidine-3-carboxyl-azetidine-2-carboxyl-aspartyl-isoleucine;
N-amidinopyrrolidine-3-carboxyl-prolyl-aspartyl-valine;
N-amidinopyrrolidine-3-carboxyl-prolyl-aspartyl-leucine;
N-amidinopyrrolidine-3-carboxyl-prolyl-aspartyl-isoleucine;
N-amidinopyrrolidine-3-carboxyl-piperidine-2-carboxyl-aspartyl-valine;
N-amidinopyrrolidine-3-carboxyl-piperidine-2-carboxyl-aspartyl-leucine;
N-amidinopyrrolidine-3-carboxyl-piperidine-2-carboxyl-aspartyl-isoleucine;
piperidine-4-carboxyl-azetidine-2-carboxyl-aspartyl-valine;
piperidine-4-carboxyl-azetidine-2-carboxyl-aspartyl-leucine;
piperidine-4-carboxyl-azetidine-2-carboxyl-aspartyl-isoleucine;
piperidine-4-carboxyl-prolyl-aspartyl-valine;
piperidine-4-carboxyl-prolyl-aspartyl-leucine;
piperidine-4-carboxyl-prolyl-aspartyl-isoleucine;
piperidine-4-carboxyl-piperidine-2-carboxyl-aspartyl-valine;
piperidine-4-carboxyl-piperidine-2-carboxyl-aspartyl-leucine;
piperidine-4-carboxyl-piperidine-2-carboxyl-aspartyl-isoleucine;

N-amidinopiperidine-4-carboxyl-azetidine-2-carboxyl-aspartyl-valine;
N-amidinopiperidine-4-carboxyl-azetidine-2-carboxyl-aspartyl-leucine;
N-amidinopiperidine-4-carboxyl-azetidine-2-carboxyl-aspartyl-isoleucine;
N-amidinopiperidine-4-carboxyl-prolyl-aspartyl-valine;
N-amidinopiperidine-4-carboxyl-prolyl-aspartyl-leucine;
N-amidinopiperidine-4-carboxyl-prolyl-aspartyl-isoleucine;
N-amidinopiperidine-4-carboxyl-piperidine-2-carboxyl-aspartyl-valine;
N-amidinopiperidine-4-carboxyl-piperidine-2-carboxyl-aspartyl-leucine; and
N-amidinopiperidine-4-carboxyl-piperidine-2-carboxyl-aspartyl-isoleucine.

Compounds of the present invention were tested for inhibition of platelet aggregation using the following procedures:

I. Inhibition of Radiolabeled ($^{125}$I) Fibrinogen Binding Assay, which is essentially based on the method described in Proc. Natl. Acad. Sci. USA Vol. 83, pp. 5708–5712, August 1986, and is as follows.

Platelets are washed free of plasma constituents by the albumin density-gradient technique. In each experimental mixture platelets in modified Tyrode's buffer are stimulated with human α-thrombin at 22°–25° C. for 10 minutes ($3.125 \times 10''$ platelets per liter and thrombin at 01 N1H units/ml). Hirudin is then added at a 25-fold excess for 5 minutes before addition of the radiolabeled ligand and any competing ligand. After these additions, the final platelet count in the mixture is $1 \times 10''$/liter. After incubation for an additional 30 minutes at 22°–25° C., bound and free ligand are separated by centrifuging 50 μl of the mixture through 300 μl of 20% sucrose at 12,000×g for 4 minutes. The platelet pellet is then separated from the rest of the mixture to determine platelet-bound radioactivity. Nonspecific binding is measured in mixtures containing an excess of unlabeled ligand. When binding curves are analyzed by Scatchard analysis, nonspecific binding is derived as a fitted parameter from the binding isotherm by means of a computerized program. To determine the concentration of each inhibitory compound necessary to inhibit 50% of fibrinogen binding to thrombin-stimulated platelets (IC$_{50}$), each compound is tested at 6 or more concentrations with $^{125}$I-labeled fibrinogen held at 0.176 μmol/liter (60 μg/ml). The IC$_{50}$ is derived by plotting residual fibrinogen binding against the logarithm of the sample compound's concentration.

II. Inhibition of Fibrinogen—Mediated Platelet Aggregation, which is essentially based on the method described in Blood, Vol. 66, No. 4, October 1985, pp. 946–952, and is as follows.

Human Platelets were isolated from freshly drawn whole blood and were suspended in 0.14 mol/L NaCl, 2.7 mmol/L KII, 12 mmol/L NaHCO$_3$, 0.42 mmol/L Na$_2$HPO$_4$, 0.55 mmol/L glucose, and 5 mmol/L Hepes, pH 7.35 at $2 \times 10^8$ platelets/ml. The suspension was incubated at 37° C. An aliquot of 0.4 ml of platelet suspension was activated by human thrombin at a final concentration of 2 μg/ml of thrombin for one minute. After one minute the reaction was stopped by a thrombin inhibitor. Serial dilution of the compound being tested was then added to the activated platelet, the reaction was allowed to proceed for one minute, followed by the addition of human fibrinogen at a final concentration of 60 μ/ml of fibrinogen. Platelet aggregation was then recorded by an aggregometer. Rate of aggregation was used to calculate IC$_{50}$.

Representative results of platelet aggregation inhibition are shown in Table I.

TABLE I

| | Inhibition of $^{125}$I-Fibrinogen Binding IC$_{50}$ (μM) | Inhibition of Fibrinogen Mediated Platelet Aggregation IC$_{50}$ (μM) | % inhibition at 25 μM |
|---|---|---|---|
| N-[2(S)-1-(piperidin-4-yl-carbonyl)azetidin-2-yl-carbonyl]-L-aspartyl-L-valine | >64 | 29.6 | 47 |
| N-[2(S)-1-(1-amidinopiperidin-4-yl-carbonyl)-azetidin-2-yl-carbonyl]-L-aspartyl-L-valine | * | >200 | 15 |

*This compound inhibited binding to the extent of 15% at 25 μM.

The compounds of the present invention may be orally or parenterally administered to mammals. The compound may be incorporated into pharmaceutical formulations having excipients suitable for these administrations and which do not adversely react with the compounds, for example, water, vegetable oils, certain alcohols and carbohydrates, gelatin and magnesium stearate. The pharmaceutical formulations containing an active compound of the present invention may be made into: tablets, capsules, elixirs, drops or suppositories for enteral administration; and solutions, suspensions or emulsions for parenteral administration.

In general, compound of this invention is administered in dosages of approximately 1 to 200 mg per dosage unit or higher. The daily dosage is approximately 0.02–5 mg/kg of body weight. It is to be understood, however, that the particular dose for each patient as usually depends on very diverse factors, such as the age, body weight, general condition of health, sex, diet and the like of the patient, on the time and route of administration, on the rate of excretion, on the combination of medicaments and on the severity of the disease.

Having described the invention, it will be apparent to one of ordinary skill in the art that changes and modifications can be made thereto without departing from the spirit and scope of the invention as set forth herein.

What is claimed is:

1. A compound of the formula

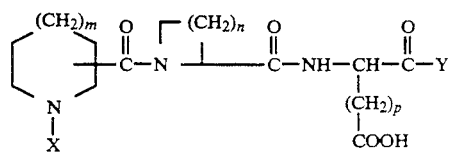

wherein:
X is H, amidino,

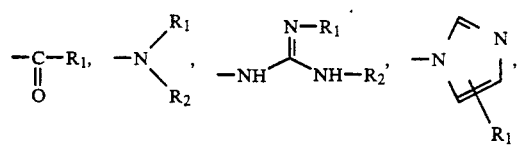

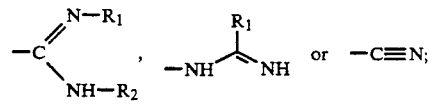

Y is —OR$_1$,

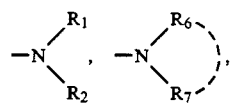

a D- or L-amino acid or its corresponding carboximide, a synthetic amino acid of the formula

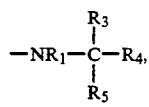

a dipeptide or a dipeptide isostere of the formula

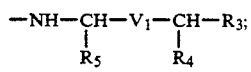

R$_1$ and R$_2$ are independently H, alkyl, aryl, aralkyl, or allyl;

R$_3$ is H, —CO$_2$H, —CO$_2$R$_1$, —CONH$_2$,

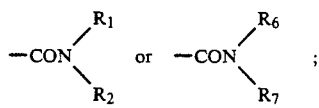

R$_4$ and R$_5$ are independently H, alkyl, cycloalkyl, cycloalkylmethyl,

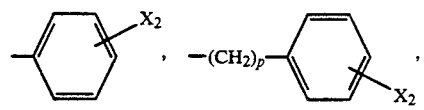

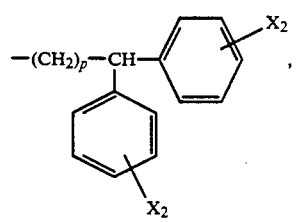

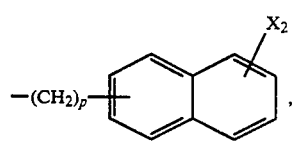

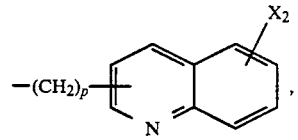

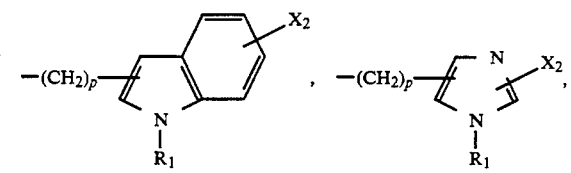

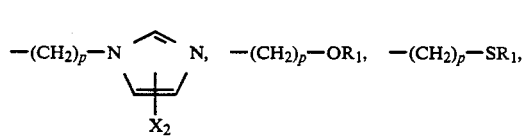

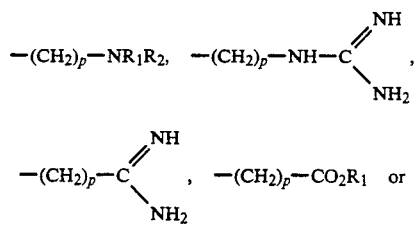

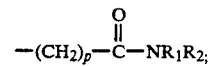

p is 0 to 8;

R$_6$ and R$_7$ form a ring with the nitrogen to which they are attached and are —(CH$_2$)$_4$—, (CH$_2$)$_5$—, —(CH$_2$)$_6$—, —CH$_2$CH$_2$OCH$_2$CH$_2$—, —CH$_2$CH$_2$NR$_1$CH$_2$— or

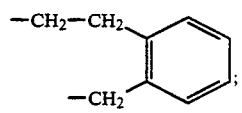

X$_2$ is H, Cl, Br, F, —OR$_1$, —NO$_2$,

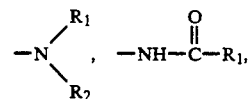

p1  —SR$_1$, C$_1$-C$_5$ alkyl, phenyl, —CO$_2$R$_1$,

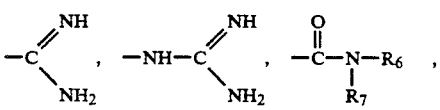

—CF$_3$ or —NHSO$_2$R$_1$;

V$_1$ is

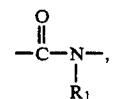

—(CH$_2$)$_n$—, —CH=CH—, —CH$_2$—NH—, —CH$_2$—O—, —CH$_2$—S— or

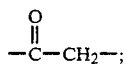

m is 0, 1 or 2;
n is 0, 1, 2 or 3; and
p is 0, 1, 2 or 3; or
pharmaceutically acceptable salts thereof.

2. A compound of claim 1 wherein said D- or L-amino acid is selected from the group consisting of: Asp, Arg, Ala, Asn, Cys, Gly, Glu, Gln, His, Ile, Leu, Lys, Met, Orn, Phe, Pro, Ser, Thr, Trp, Tyr and Val.

3. A compound of claim 1 wherein:
$R_1$ and $R_2$ are independently hydrogen or phenyl;
$R_3$ is H or —$CO_2H$;
$R_4$ and $R_5$ are independently H, alkyl or cycloalkyl;
m is 1;
n is 0;
p is 1; and
$R_6$ and $R_7$ are —$(CH_2)_4$— forming a ring with the nitrogen to which they are attached.

4. A stereoisomeric compound of claim 1.

5. A diastereomeric compound of claim 1.

6. A pharmaceutical composition for the treatment of thrombus formation in a mammal in need of such treatment comprising a pharmaceutically acceptable carrier and a pharmaceutically active amount of a compound of claim 1.

7. A method of treating thrombus formation in a mammal comprising the administration of a composition of claim 6.

8. A compound according to claim 1 selected from the group consisting of:
pyrrolidine-3-carboxyl-azetidine-2-carboxyl-aspartyl-valine;
pyrrolidine-3-carboxyl-azetidine-2-carboxyl-aspartyl-leucine;
pyrrolidine-3-carboxyl-azetidine-2-carboxyl-aspartyl-isoleucine; and
pyrrolidine-3-carboxyl-prolyl-aspartyl-valine.

9. A compound according to claim I selected from the group consisting of:
pyrrolidine-3-carboxyl-prolyl-aspartyl-leucine;
pyrrolidine-3-carboxyl-prolyl-aspartyl-isoleucine;
pyrrolidine-3-carboxyl-piperidine-2-carboxyl-aspartyl-valine; and
pyrrolidine-3-carboxyl-piperidine-2-carboxyl-aspartyl-leucine.

10. A compound according to claim 1 selected from the group consisting of:
pyrrolidine-3-carboxyl-piperidine-2-carboxyl-aspartyl-isoleucine;
N-amidinopyrrolidine-3-carboxyl-azetidine-2-carboxyl-aspartyl-valine;
N-amidinopyrrolidine-3-carboxyl-azetidine-2-carboxyl-aspartyl-leucine; and
N-amidinopyrrolidine-3-carboxyl-azetidine-2-carboxyl-aspartyl-isoleucine.

11. A compound according to claim 1 selected from the group consisting of:
N-amidinopyrrolidine-3-carboxyl-prolyl-aspartyl-valine;
N-amidinopyrrolidine-3-carboxyl-prolyl-aspartyl-leucine;
N-amidinopyrrolidine-3-carboxyl-prolyl-aspartyl-isoleucine; and
N-amidinopyrrolidine-3-carboxyl-piperidine-2-carboxyl-aspartyl-valine.

12. A compound according to claim 1 selected from the group consisting of:
N-amidinopyrrolidine-3-carboxyl-piperidine-2-carboxyl-aspartyl-leucine;
N-amidinopyrrolidine-3-carboxyl-piperidine-2-carboxyl-aspartyl-isoleucine;
piperidine-4-carboxyl-azetidine-2-carboxyl-aspartyl-valine; and
piperidine-4-carboxyl-azetidine-2 -carboxyl-aspartyl-leucine.

13. A compound according to claim 1 selected from the group consisting of:
piperidine-4-carboxyl-azetidine-2-carboxyl-aspartyl-isoleucine;
piperidine-4-carboxyl-prolyl-aspartyl-valine;
piperidine-4-carboxyl-prolyl-aspartyl-leucine; and
piperidine-4-carboxyl-prolyl-aspartyl-isoleucine.

14. A compound according to claim 1 selected from the group consisting of:
piperidine-4-carboxyl-piperidine-2-carboxyl-aspartyl-valine;
piperidine-4-carboxyl-piperidine-2-carboxyl-aspartyl-leucine;
piperidine-4-carboxyl-piperidine-2-carboxyl-aspartyl-isoleucine; and
N-amidinopiperidine-4-carboxyl-azetidine-2-carboxyl-aspartyl-valine.

15. A compound according to claim 1 selected from the group consisting of:
N-amidinopiperidine-4-carboxyl-azetidine-2-carboxyl-aspartyl-leucine;
N-amidinopiperidine-4-carboxyl-azetidine-2-carboxyl-aspartyl-isoleucine;
N-amidinopiperidine-4-carboxyl-prolyl-aspartyl-valine; and
N-amidinopiperidine-4-carboxyl-prolyl-aspartyl-leucine.

16. A compound according to claim 1 selected from the group consisting of:
N-amidinopiperidine-4-carboxyl-prolyl-aspartyl-isoleucine;
N-amidinopiperidine-4-carboxyl-piperidine-2-carboxyl-aspartyl-valine;
N-amidinopiperidine-4-carboxyl-piperidine-2-carboxyl-aspartyl-leucine; and
N-amidinopiperidine-4-carboxyl-piperidine-2-carboxyl-aspartyl-isoleucine.

* * * * *